(12) United States Patent
Park et al.

(10) Patent No.: US 10,159,463 B2
(45) Date of Patent: Dec. 25, 2018

(54) ULTRASOUND PROBE

(71) Applicant: SAMSUNG MEDISON CO., LTD., Hongcheon-gun, Gangwon-do (KR)

(72) Inventors: Moon Kyu Park, Incheon (KR); Jong Sik Kim, Seoul (KR); Gil Ju Jin, Seoul (KR); Jeong Un Yoon, Incheon (KR)

(73) Assignee: SAMSUNG MEDISON CO., LTD., Hongcheon-Gun, Gangwon-Do (KR)

(*) Notice: Subject to any disclaimer, the term of this patent is extended or adjusted under 35 U.S.C. 154(b) by 644 days.

(21) Appl. No.: 14/478,880

(22) Filed: Sep. 5, 2014

(65) Prior Publication Data

US 2015/0065887 A1 Mar. 5, 2015

(30) Foreign Application Priority Data

Sep. 5, 2013 (KR) .................. 10-2013-0106773

(51) Int. Cl.
*A61B 8/12* (2006.01)
*A61B 8/00* (2006.01)

(52) U.S. Cl.
CPC ............. *A61B 8/12* (2013.01); *A61B 8/4281* (2013.01); *A61B 8/4455* (2013.01); *A61B 8/4461* (2013.01)

(58) Field of Classification Search
CPC ....... A61B 8/12; A61B 8/4461; A61B 8/4455; A61B 8/4281
See application file for complete search history.

(56) References Cited

U.S. PATENT DOCUMENTS

| | | | | |
|---|---|---|---|---|
| 5,372,138 A | * | 12/1994 | Crowley | A61B 5/416 600/463 |
| 5,720,287 A | * | 2/1998 | Chapelon | A61B 8/12 600/439 |
| 2007/0066902 A1 | * | 3/2007 | Wilser | A61B 8/12 600/459 |

* cited by examiner

*Primary Examiner* — Peter Luong
(74) *Attorney, Agent, or Firm* — McDermott Will & Emery LLP

(57) ABSTRACT

An ultrasound probe including a housing, a head part provided on the housing so as to enable expansion and contraction, an array provided in the housing and having one or more transducers, a rotary part provided at a rear surface of the array to rotate the array, a pressing part configured to expand the head part by applying pressure to the head part, and a control part, when the head part is inserted into a target object, configured to allow the array to control the pressing part such that the head part is expanded, and allow the array to be rotated in the expanded head part, by controlling the rotary part, thereby relieving pain involved with insertion of the ultrasound probe.

14 Claims, 12 Drawing Sheets

ULTRASOUND PROBE

CROSS-REFERENCE TO RELATED APPLICATION

This application claims the benefit of Korean Patent Applications No. 2013-0106773, filed on Sep. 5, 2013 in the Korean Intellectual Property Office, the disclosure of which is incorporated herein by reference.

BACKGROUND

1. Field

Embodiments of the present disclosure relate to an ultrasound probe for generating an ultrasound image of a target object having the ultrasound probe inserted thereinto, by use of an ultrasound wave.

2. Description of the Related Art

An ultrasound diagnosis apparatus irradiates ultrasound waves toward a target region of the interior of a body of a target object from the surface of the target object to acquire an image regarding soft tissue tomograms or a blood stream based on information of a reflected ultrasound signal (an ultrasound echo signal) using a non-invasive method. The ultrasound diagnosis apparatus is small and inexpensive when compared to other image diagnosis apparatuses, such as an X-ray diagnosis apparatus, a computerized tomography (CT) scanner, a magnetic resonance imager (MRI), and a nuclear medicine diagnosis apparatus, and is capable of displaying a diagnosis image in real time. In addition, the ultrasound diagnosis apparatus has a high security against radiation exposure, and is thus widely used for heart, abdomen, and urinary system and in obstetrics and gynecology.

The ultrasound diagnosis apparatus includes an ultrasound probe transmitting ultrasound signals to a target object and receiving an ultrasound echo signal reflected by the target object to acquire an image of the interior of the target object.

Meanwhile, the ultrasound probe includes a transducer. The transducer includes a piezoelectric layer in which a piezoelectric material vibrates to execute conversion between an electrical signal and an acoustic signal, a matching layer reducing an acoustic impedance difference between the piezoelectric layer and the target object so as to maximally transmit ultrasound waves generated from the piezoelectric layer to the object, a lens layer concentrating ultrasound waves proceeding in the forward direction of the piezoelectric layer on a predetermined point, and a backing layer preventing ultrasound waves from proceeding in the backward direction of the piezoelectric layer to prevent image distortion.

SUMMARY

Therefore, it is an aspect of the present disclosure to provide an ultrasound probe that is expanded after being inserted into a target object to perform an ultrasound test.

Additional aspects of the disclosure will be set forth in part in the description which follows and, in part, will be obvious from the description, or may be learned by practice of the disclosure.

In accordance with an aspect of the present disclosure, an ultrasound probe includes a housing, a head part, an array, a rotary part, a pressing part and a control part. The head part may be provided on the housing so as to enable expansion and contraction. The array may be provided in the housing and have one or more transducers. The rotary part may be provided at a rear surface of the array to rotate the array. The pressing part may be configured to expand the head part by applying pressure to the head part. The control part, when the head part is inserted into a target object, may be configured to allow the array to control the pressing part such that the head part is expanded, and allow the array to be rotated in the expanded head part, by controlling the rotary part.

The head part may be replaceable. In addition, the head part may be mounted at an inside of the housing. The head part may be provided in the form of a convex lens at an opening of the housing, and may be expanded in the form of a balloon.

The pressing part may expand the head part by use of a fluid. In addition, the housing may be separated into an upper portion housing and a lower portion housing by a partition wall, and the pressing part may apply pressure only to the upper portion housing.

The array may have a width larger than a diameter of the housing. The transducers of the array may be arranged in a matrix form, a linear form, a convex form or a concave form.

The array may be separated into a plurality of arrays. The separated arrays may be coupled to each other in the head part. Each of the separated arrays may be provided with a rotary part.

The ultrasound probe may further include a support member coupled to the rotary part, and a driving part moving the support member forward or backward. The control part may control the rotary part such that the support part rotates in the head part after proceeding forward by a predetermined distance.

The ultrasound probe may further include a support member coupled to the rotary part and including one or more rotatable joints.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1A:
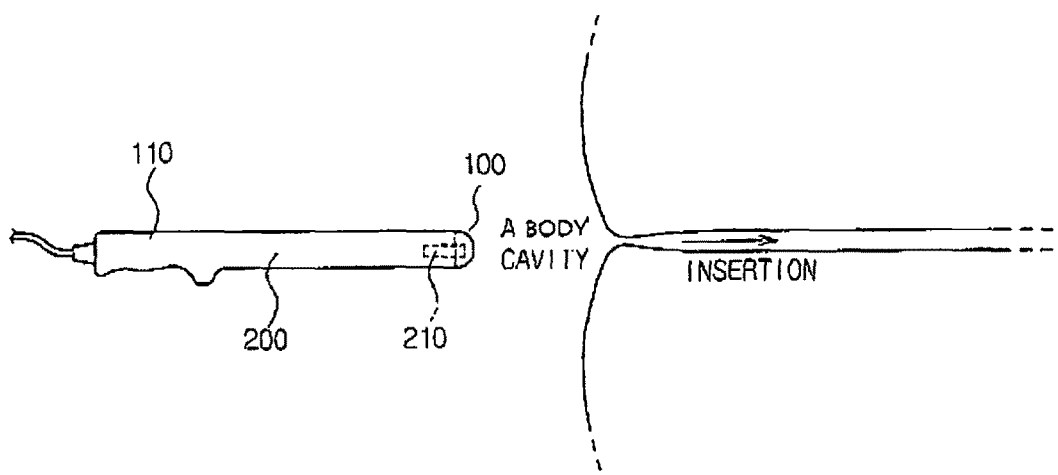
FIGS. 1A and 1B are conceptual views illustrating an ultrasound probe.

Reference will now be made in detail to the embodiments of the present disclosure, examples of which are illustrated in the accompanying drawings, wherein like reference numerals refer to like elements throughout.

Figure 1B:
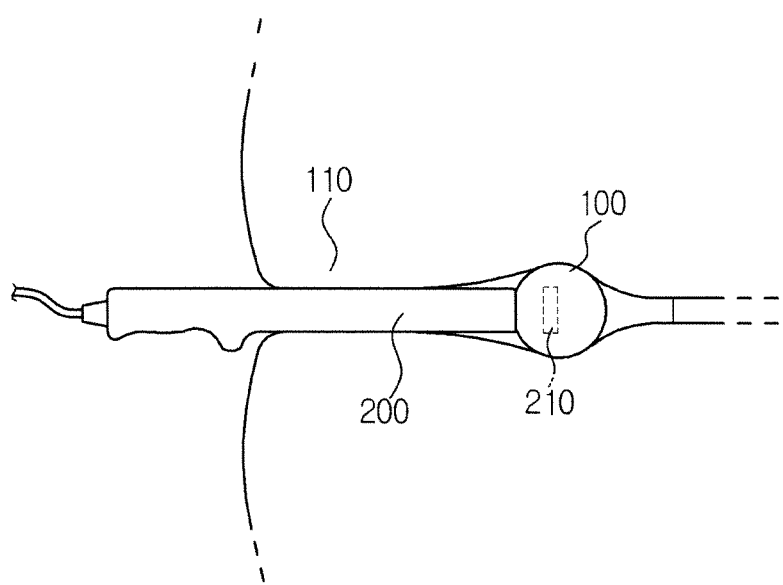

FIGS. 1A and 1B are conceptual views illustrating an ultrasound probe. In detail, FIG. 1A is a conceptual view illustrating the ultrasound probe before being inserted into a target object, and FIG. 1B is a conceptual view illustrating the ultrasound probe after being inserted into a target object.

Referring to FIGS. 1A and 1B, an ultrasound probe in accordance with an embodiment of the present disclosure generates an ultrasound image after being inserted into a target object. For example, the ultrasound probe may be inserted into a body cavity, an anus and a vagina of a human body.

The ultrasound probe includes a head part 100 configured to enable expansion and a housing 110. As shown in FIG. 1A, an array 210 is located at a housing interior 200 of the ultrasound probe as a dotted line. In this case, the array 210 has a width larger than a diameter of the housing interior 200. As shown in FIG. 1B, the head part 100 is expanded after the ultrasound probe is inserted into the target object, and an ultrasound image is acquired as the array 210 rotates in the expanded head part 100. Since the ultrasound probe is provided with the head part 100 expanded after being inserted into the target object, and with the array 210 rotating in the expanded head part 100, the ultrasound probe is provided in a smaller size. In addition, the head part 100 is expanded after the ultrasound probe is inserted to generate an ultrasound image, thereby minimizing a discomfort caused to the target object when the ultrasound probe is inserted. In addition, the ultrasound probe uses the array 210 having a width larger than the diameter of the housing 110, thereby obtaining a more sophisticated and wider view of ultrasound images.

Hereinafter, the ultrasound probe in accordance with an embodiment of the present disclosure will be described in detail.

Figure 2:
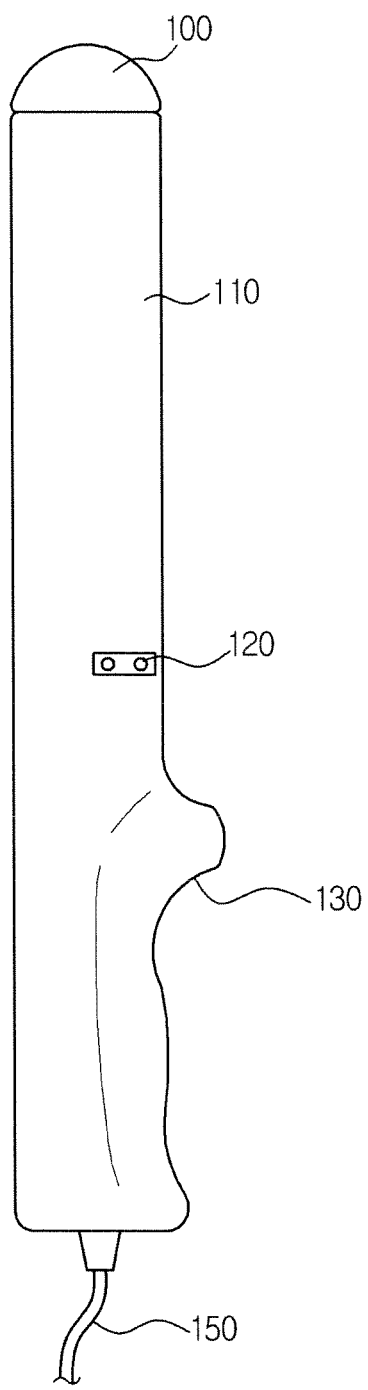
FIG. 2 is a perspective view illustrating an exterior of the ultrasound probe before being inserted into a target object in accordance with an embodiment of the present disclosure.

FIG. 2 is a perspective view illustrating an exterior of the ultrasound probe before being inserted into a target object in accordance with an embodiment of the present disclosure.

Referring to FIG. 2, the exterior of the ultrasound probe includes a head part, a housing, an input part and a cable.

The head part 100 may be expanded by receiving a pressure so as to form a space in which the array may rotate. Accordingly, the head part 100 may include an elastic material that may be expanded by pressure. The head part 100 may include material that is not harmful to a target object while having an acoustic impedance similar to that of a skin of the human body, an acoustic attenuation constant equal to or lower than that of a soft tissue of the human body, and an electric conductivity equal to or lower than that of silicon. In addition, the head part 100 may be provided on the housing 110 so as to be easily replaced.

Meanwhile, the head part 100 is provided on the housing 110. In detail, the housing 110 has an opening at which the head part 100 is provided. In this case, the head part 100 comes into close contact with the opening to prevent fluid from flowing out and body liquid from entering. In addition, the housing 100 is provided at a lower end thereof with a handle 130 for a user to grip.

The input part 120 receives various control signals from a user of the ultrasound probe. The control signal represents various signals to control the operation of the ultrasound probe, and may be generated by a user's input. The input part 120 may be provided at one portion of the housing 110. Meanwhile, although the input part 120 on FIG. 2 is illustrated on the ultrasound probe, the input part 120 may be located outside the ultrasound probe in the same manner as a control panel of the ultrasound apparatus.

Figure 3:
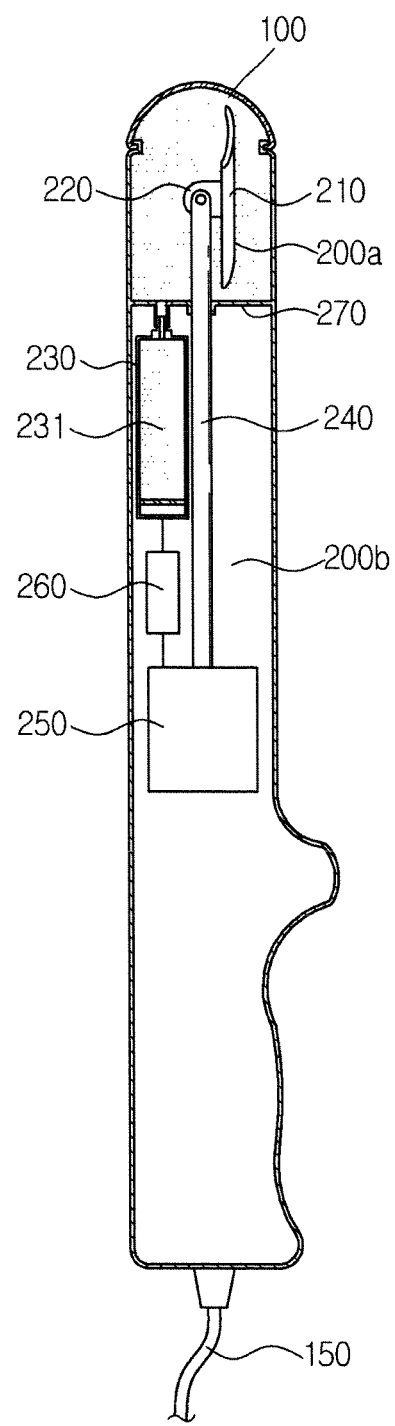
FIG. 3 is a conceptual cross sectional view illustrating an interior of the ultrasound probe before being inserted into a target object in accordance with an embodiment of the present disclosure.

FIG. 3 is a conceptual cross sectional view illustrating an interior of the ultrasound probe before being inserted into a target object in accordance with an embodiment of the present disclosure.

Referring to FIG. 3, the interior of the ultrasound probe includes an array, a rotary part, a pressing part, a support member, a driving part, a control part and a partition wall.

The array 210 may include one or more transducers. The array 210 acquires an ultrasound image based on the one or more transducers. Here, the ultrasound transducer may be implemented using various transducers, for example, a magnetostrictive ultrasound transducer using a magnetostrictive effect of ferrite material, which is mainly used in a conventional ultrasound probe, a piezoelectric ultrasound transducer using a piezoelectric effect of a piezoelectric material, or a capacitive micromachined ultrasound transducer (cMUT), which transmits and receives ultrasound waves using vibration of several hundreds or several thousands of micromachined thin films. Meanwhile, the transducers of the array 210 may be arranged in a matrix form, a linear form, a convex form and a concave form to acquire an ultrasound image. In addition, the array 210 may generate a three dimensional ultrasound image based on the one or more transducers. In addition, the array 210 may have a width larger than a diameter of the housing 110, thereby generating a wider angle of ultrasound image or sophisticated ultrasound image.

The rotary part 220 may rotate the array 210. In detail, the rotary part 220 is provided at a rear surface of the array 210 to rotate the array 210 in the head part 100 expanded. The rotary part 220 rotates the array 210 in various methods. For example, the rotary part 220 may include a motor generating a driving force and a gear coupled to the array 210 to transmit the driving force of the motor, to rotate the array 210. In this case, the motor may include a stepping motor that may control an angle of rotation.

The pressing part 230 may allow the head part 100 to be expanded or contracted by adjusting the pressure of the head part 100. In detail, the pressing part 230 may allow the head part 100 to be expanded by injecting a fluid into the ultrasound probe to increase the pressure of the head part 100. In addition, the pressing part 230 may allow the head part 100 to be contracted again by suctioning a fluid in the ultrasound probe to decrease the pressure of the head part 100. The pressing part 230 may include a storage member 231 to additionally accommodate a fluid. Meanwhile, the pressing part 230 may adjust the pressure of the head part 100 by use of a fluid separately provided outside the ultrasound probe. Here, the fluid needs to be harmful to a target object in case of an accident of leakage of the fluid. The fluid has an acoustic impedance similar to that of the skin of the human body, an acoustic attenuation constant equal to or lower than that of the soft tissue and an electric conductivity equal to or lower than that of the silicon. For example, the fluid may include an oil used in the ultrasound probe.

Meanwhile, the ultrasound probe may have a partition wall 270. The partition wall 270 separates the housing interior 200 into an upper portion housing 200a and a lower portion housing 200b. In this case, the partition wall 270 completely separates the housing interior 200 into the upper portion housing 200a and the lower portion housing 200b to block fluid from moving between the upper portion housing 200a and the lower portion housing 200b. Accordingly, the pressing part 230 may adjust the pressure of the head part 100 by use of a smaller amount of fluid, enabling expansion and contraction of the head part 100 by use of a smaller amount of fluid. In addition, the partition wall 270 may prevent the components, such as the control part 260 or the driving part 250 of the lower portion housing 200b from being exposed to the pressure of the fluid.

The support member 240 supports the rotary part 220 and is coupled to the rotary part 220. A lower end of the support member 240 may be coupled to the driving part 250. The driving part 250 may allow the support member 240 to move back and forth or rotate. For example, the support member 240 is geared to the driving part 250, and the driving part 250 allows the support member 240 to move back and forth or rotate based on a driving force of the motor. In addition, although the driving part 250 is illustrated as serving to allow the support member 240 to move forward/backward as well as rotate in FIG. 3, a driving part allowing the support member 240 to move forward/backward may be separately provided from a driving part allowing the support member 240 to rotate. Meanwhile, the support member 240 may accommodate various components, such as a wire to supply an electric energy to the array 210 or the rotary part 220 or a wire to transmit and receive data to/from the array 210 or the rotary part 220. In this case, the driving part 250 may include one or more stepping motors and gears to control the angle of rotation.

The control part 260 receives a control signal and controls the rotary part 220, the pressing part 230 and the driving par 250 based on the received control signal, to acquire an ultrasound image. In this case, the control signal may be input by a user or may be generated by information detected from one or more sensors.

Hereinafter, the control part 260 will be described in detail with reference to FIGS. 4 and 5.

Figure 4:
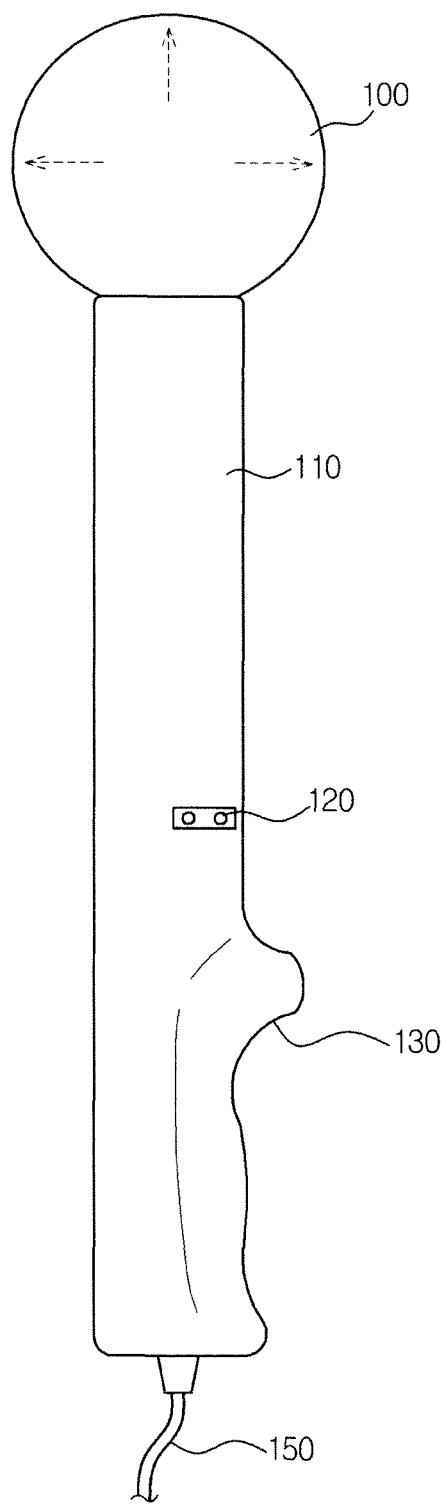
FIG. 4 is a perspective view illustrating an exterior of the ultrasound probe after being inserted into a target object in accordance with an embodiment of the present disclosure.

FIG. 4 is a perspective view illustrating an exterior of the ultrasound probe after being inserted into a target object in accordance with an embodiment of the present disclosure.

Figure 5:
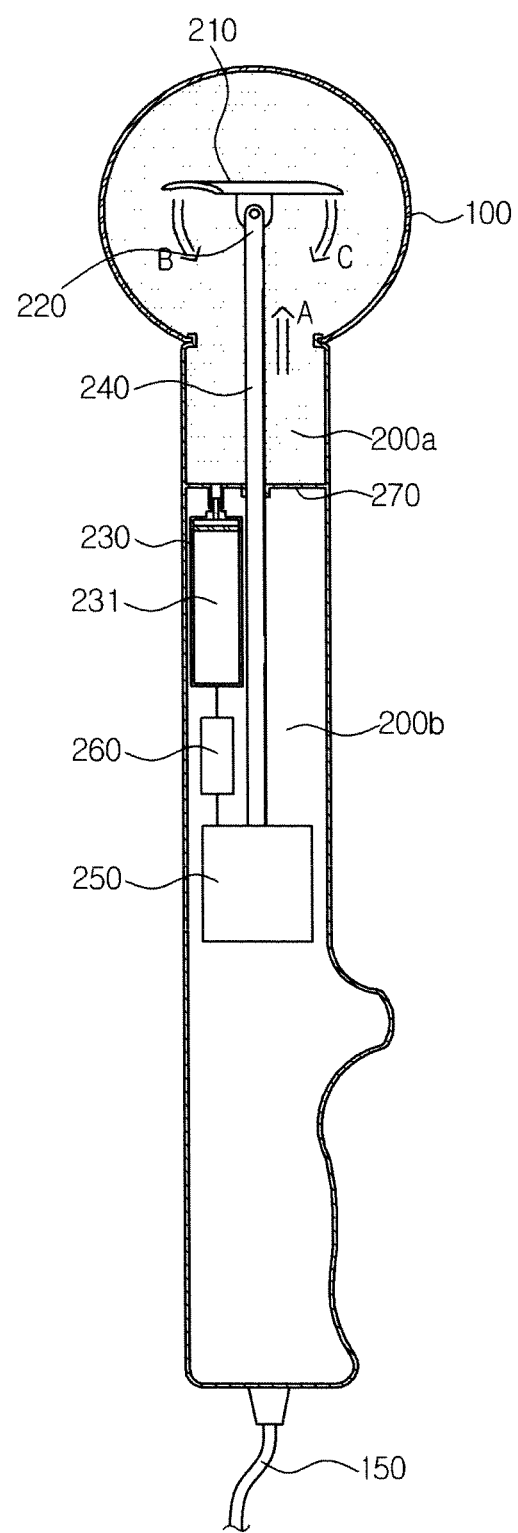
FIG. 5 is a cross sectional view illustrating an interior of the ultrasound probe after being inserted into a target object in accordance with an embodiment of the present disclosure.

FIG. 5 is a conceptual cross sectional view illustrating an interior of the ultrasound probe after being inserted into a target object in accordance with an embodiment of the present disclosure.

Referring FIG. 3, the array 210 of the ultrasound probe is located in the housing 110 before being inserted into the human body. Accordingly, the width of the housing 110 is not dependent of the size of the array 210.

Referring to FIGS. 4 and 5, the control part 260 controls the rotary part 220, the pressing part 230 and the driving part 250 to output an ultrasound image. The control part 260 may provide a user with ultrasound wave images of various angles and directions by controlling the rotary part 220, the pressing part 230 and the driving part 250 according to the signal input by the user of the ultrasound probe.

In more detail, as the head part 100 of the ultrasound probe is inserted into a target object, the control part 260 may inject a fluid stored in the storage member 231 into the upper portion housing 200a by controlling the pressing part 230. As the fluid is injected into the upper portion housing 200a, the pressure of the upper portion housing 200a is increased, and the head part 100 formed of elastic material is expanded in the form of a balloon as shown in FIG. 4 due to the increase of the pressure. In this case, the head part 100 may expanded in a varied degree depending on the amount of fluid being injected. Meanwhile, the control unit 260 may adjust the speed and amount of fluid being injected by controlling the pressing part 230. For example, the control part 260 may control the pressing part 230 such that a predetermined amount of fluid is injected at a predetermined speed, or a fluid is injected according to an input signal by a user. In addition, when a fluid is injected, the control part 260 monitors the pressure of the upper portion housing 200a and stops injecting fluid if the monitored pressure exceeds a predetermined pressure, thereby preventing an accident.

In addition, the control part 260 may allow the array 210 to be rotated in the head part 100 that is expanded by controlling the driving part 250 such that the support part 240 moves forward in direction A. In this case, the distance by which the support member 240 is moved by the driving part 250 may vary with the size of the array 210. That is, the control part 260 controls the driving part 250 such that the support member 240 moves forward in direction A by a predetermined distance, thereby enabling the array 210 to be rotated by the rotary part 220 in the expanded head part 100. Meanwhile, if the array 210 may be able to be rotated by the rotary part 220 in the expanded head part 100 without the support member 240 moving forward, the control part 260 may not move the support member 240.

In addition, the control part 260 may control the rotary part 220 to rotate the array 210. In more detail, the control part 260 controls the array 210 to rotate in a direction B such that an ultrasound image of a front of the ultrasound probe is acquired. In addition, the control part 260 controls the rotation of the rotary part 220 according to an input signal by a user so as to acquire an ultrasound image in a direction desired by the user. For example, according to a left side motion signal, the control part 260 controls the rotary part 220 to rotate the array 210 in a direction B such that an ultrasound image of a left side of the ultrasound probe is acquired, or according to a right side motion signal, controls the rotary part 220 to rotate the array 210 in a direction C such that an ultrasound image of a right side of the ultrasound probe is acquired.

In addition, the control part 260 controls the driving part 250 to rotate the support member 240. As the driving part 250 rotates the support member 240 according to control of the control part 260, the rotary part 220 and the array 210 that are coupled to the support member 240 are also rotated. Accordingly, the ultrasound probe may acquire an ultrasound image on the same plane in various angles. For example, the control part 260 controls the driving part 250 to rotate the support member 240 in direction D according to a rotation signal such that an ultrasound image having a different angle is acquired.

Figure 6A:
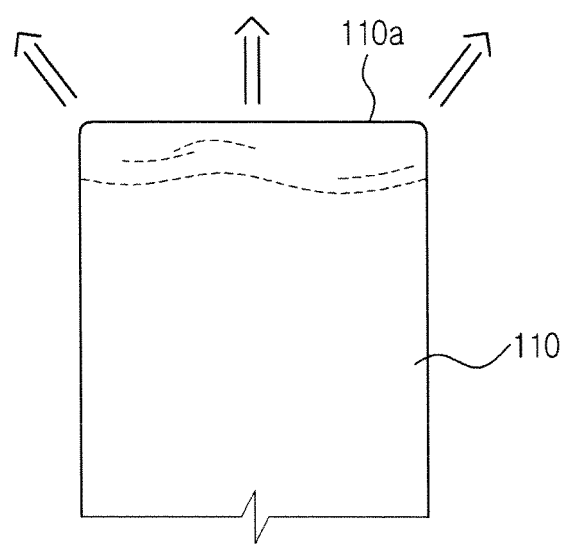
FIGS. 6A and 6B are drawings illustrating other examples of a head part of the ultrasound probe.
Figure 6B:
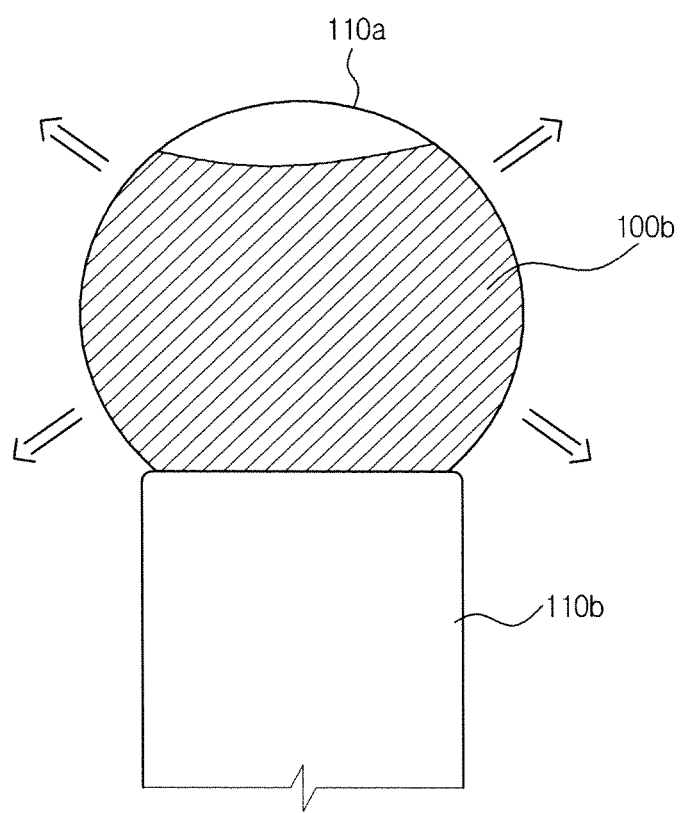

FIGS. 6A and 6B are drawings illustrating other examples of a head part of the ultrasound probe.

Although the head part 100 is provided in the form of a convex lens at a front surface of the housing 110, the present disclosure is not limited thereto. The head part may be provided on the housing 110 in various forms.

Referring to FIG. 6A, a head part 100a may be mounted at an opening of the housing 110. In detail, the head part 100a may be located inside the opening of the housing 110. In this case, the head part 100a may completely come into close contact with the housing 110. The head part 100a mounted on the opening may be expanded in a direction of an arrow on FIG. 6A by receiving pressure.

Referring to FIG. 6B, a head part 100b may be provided between an upper portion housing 110a and a lower portion housing 110b. The upper portion housing 110a, the lower portion housing 110b and the head part 100b may completely come into close contact with one another. The head part 100b may be configured to be replaceable. Meanwhile, the head part 100b provided between the upper portion housing 110a and the lower portion housing 110b may be expanded in a direction of an arrow on FIG. 6B by receiving pressure.

Meanwhile, the structure of the head part 100 is not limited thereto, and may be provided in various structures as long as the head part 100 is expandable to allow the array to be rotated therein.

Figure 7A:
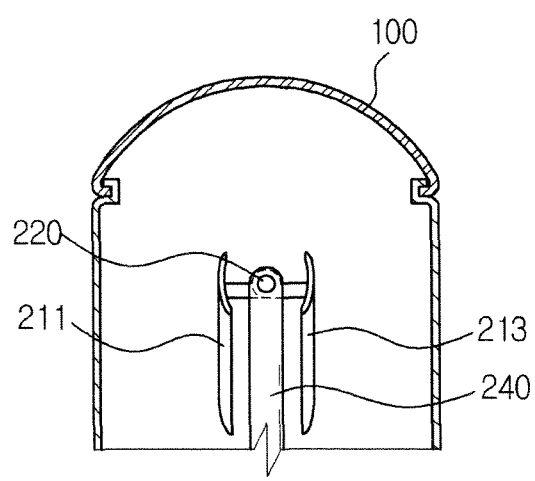
FIGS. 7A and 7B are drawings illustrating another example of an array of the ultrasound probe.
Figure 7B:
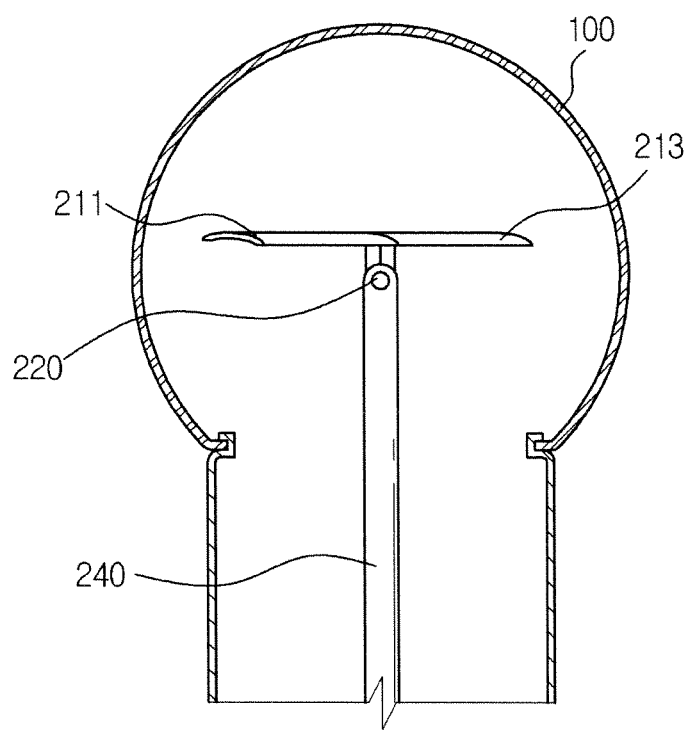

FIGS. 7A and 7B are drawings illustrating another example of the array. FIG. 7A is a conceptual cross sectional view illustrating the interior of the ultrasound probe before being inserted into a target object, and FIG. 7B is a conceptual cross sectional view illustrating the interior of the ultrasound probe after being inserted into a target object.

Referring to FIG. 7A, arrays 211 and 213 of the ultrasound probe may be provided separately from each other in the housing before the ultrasound probe is inserted into a target object. Referring to FIG. 7B, the arrays 211 and 213 having been separated are coupled in the head part 100 are expanded as the ultrasound probe is inserted into a target object, to generate an ultrasound image. The ultrasound probe may be additionally provided with rotary parts 220 configured to rotate the arrays 211 and 213, respectively, and each rotary part may allow a respective one of the arrays 211 and 213 to be coupled to each other by rotating the arrays 211 and 213 as shown in FIG. 7B. Meanwhile, although the arrays 211 and 213 are illustrated as being separated into two units in FIG. 7B, the present disclosure is not limited thereto. Arrays separated into more than two units may be provided.

Figure 8:
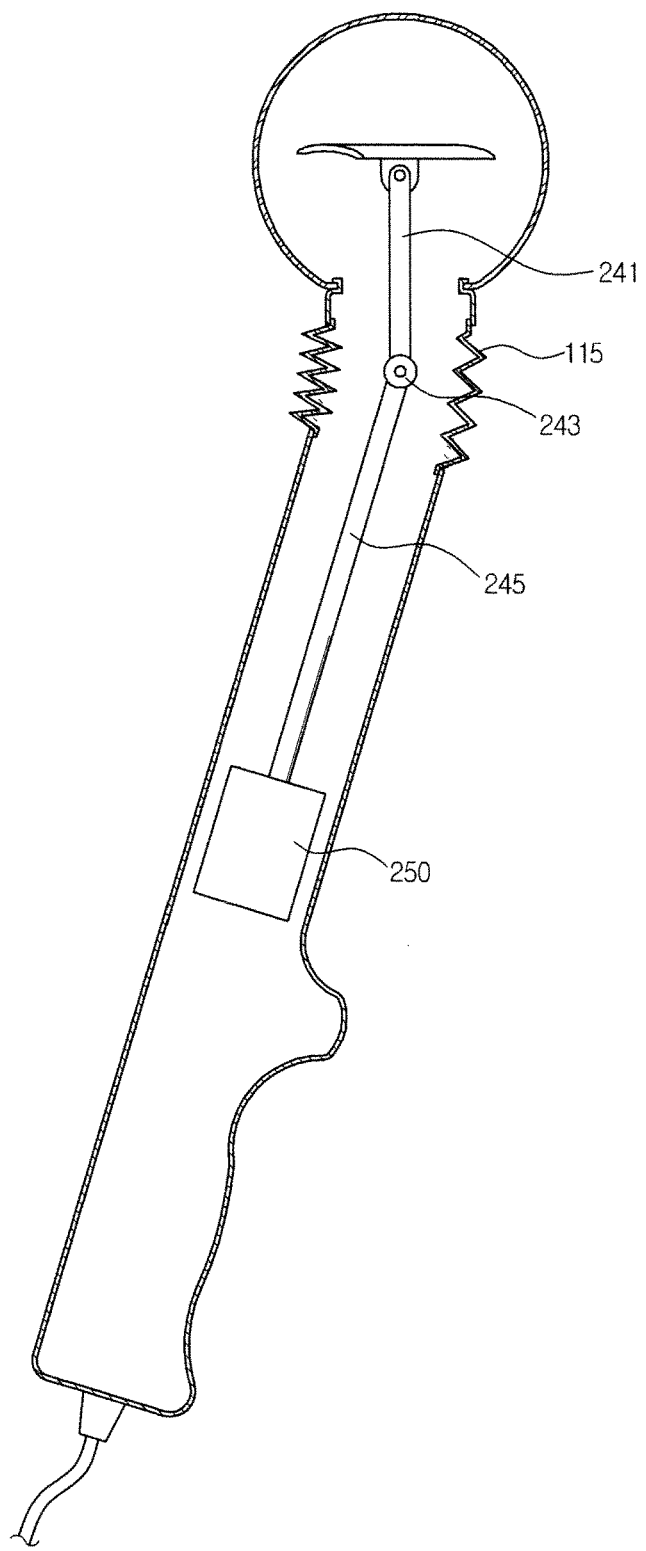
FIG. 8 is a drawing illustrating another example of a support member of the ultrasound probe.

FIG. 8 is a drawing illustrating another example of the support member of the ultrasound probe.

The support member of the ultrasound probe may have a joint. Referring to FIG. 8, the support member may include an upper portion support member 241 provided on the rotary part, a lower portion support member 245 coupled to the driving part and a joint 243 connecting the upper portion support member 241 to the lower portion support member 245. The control part 260 may control the joint 243 to move according to an input signal. The movement of the joint 243 facilitates the acquisition of the ultrasound image. In this case, a device configured to move the joint 243 may be provided on the upper portion support member 241, the lower portion support member 245 or the driving part 250. For example, the joint 243 may operate based on a driving force of a motor provided on the lower support member 245.

In this case, the housing 110 may include a wrinkle part 115. The wrinkle part 115 is located at a position corresponding to the joint 243. The wrinkle part 115 may have material or structure that enables the wrinkle part 15 to be bent. The wrinkle part 115 may move according to movement of the joint 243.

Figure 9:
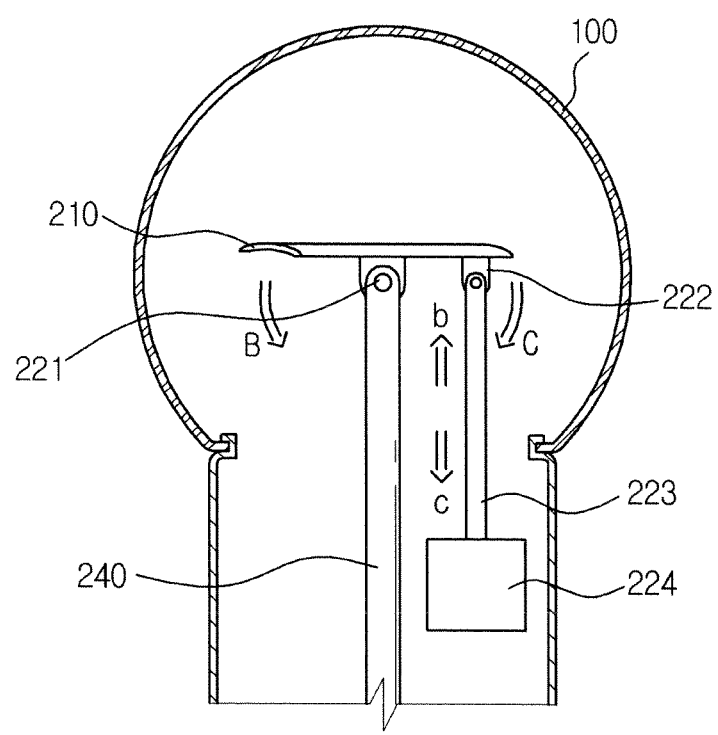
FIG. 9 is a drawing illustrating another example of a rotary part of the ultrasound probe.

FIG. 9 is a drawing illustrating another example of a rotary part of the ultrasound probe.

The rotary part according to an embodiment of the present disclosure may be provided in various structures. For example, as shown in FIG. 9, the rotary part may include a first hinge, a second hinge, a shaft and a motor.

The first hinge 221 and the second hinge 222 may be provided at a rear surface of the array 210. In this case, the first hinge 221 is provided at the center of a rear surface of the array 210, and is coupled to the support member 240. Meanwhile, the second hinge 222 may be provided at a portion between the center and an edge of the rear surface of the array 210, the second hinge 222 coupled to a shaft 223.

The shaft 223 is coupled to the motor 224 through a gear so as to perform a reciprocation motion. In this case, the motor 224 may include a stepping motor to control an angle of rotation.

The array 210 rotates by a torque generated by a reciprocating motion of the shaft 223. For example, when the shaft 223 advances in direction b by rotation of the motor 224, the array 210 rotates on the first hinge 221 in direction B. In addition, the shaft 223 retreats in direction c by rotation of the motor 224, the array 210 rotates on the first hinge 221 in direction C.

As is apparent from the above, the ultrasound probe is provided in a smaller size.

In addition, the ultrasound probe is inserted into a target object and then a head part of the ultrasound probe is expanded to acquire an ultrasound image, so that pain involved with insertion of the ultrasound probe is relieved.

In addition, an ultrasound probe having an array rotated in the expanded head part is provided so that ultrasound images having various angles and directions are provided to a user of the ultrasound probe.

In addition, an ultrasound probe having an array larger than that of a housing of the ultrasound probe is provided so that a wider view of an ultrasound image or a wider 3-D ultrasound image is provided.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound probe comprising:
    a housing;
    a head part provided on the housing so as to enable expansion and contraction;
    an array provided in the housing and having one or more transducers;
    a rotary part provided at a rear surface of the array to rotate the array;
    a pressing part configured to expand the head part by applying pressure to the head part; and
    a control part, when the head part is inserted into a target object, configured to allow the array to control the pressing part such that the head part is expanded, and allow the array to be rotated in the expanded head part, by controlling the rotary part,
    wherein the array is separated into a plurality of arrays,
    the separated arrays are coupled to each other in the head part,
    the array is movable from a first position in which each of the separated arrays has a first width smaller than a diameter of the housing to a second position in which the coupled arrays have a second width larger than the diameter of the housing,
    the rotary part includes a first rotary member and a second rotary member,
    the separated arrays include a first separated array and a second separated array, and
    the first separated array is provided with the first rotary member and the second separated array is provided with the second rotary member.

2. The ultrasound probe of claim 1, wherein the head part is replaceable.

3. The ultrasound probe of claim 1, wherein the head part is mounted at an inside of the housing.

4. The ultrasound probe of claim 1, wherein the head part is provided in the form of a convex lens at an opening of the housing.

5. The ultrasound probe of claim 1, wherein the expanded head part has a balloon shape.

6. The ultrasound probe of claim 1, wherein the pressing part expands the head part by use of a fluid.

7. The ultrasound probe of claim 1, wherein:
the housing is separated into an upper portion housing and a lower portion housing by a partition wall; and
the pressing part applies pressure only to the upper portion housing.

8. The ultrasound probe of claim 1, wherein the transducers of each of the arrays are arranged in a matrix form, a linear form, a convex form or a concave form.

9. The ultrasound probe of claim 1, wherein each of the separated arrays is provided with a rotary part.

10. The ultrasound probe of claim 1, further comprising:
a support member coupled to the rotary part; and
a driving part moving the support member forward or backward,
wherein the control part controls the rotary part such that the support member rotates in the head part after proceeding forward by a predetermined distance.

11. The ultrasound probe of claim 1, further comprising:
a support member coupled to the rotary part; and
a driving part rotating the support member,
wherein the control part controls the driving part such that the support member rotates.

12. The ultrasound probe of claim 1, further comprising a support member coupled to the rotary part and having one or more rotatable joints.

13. The ultrasound probe of claim 1, wherein the control part controls the rotary part such that a support member rotates in the head part after proceeding forward by a predetermined distance,
the predetermined distance by which the support member is moved is determined by the size of the array.

14. The ultrasound probe of claim 1, wherein the first rotary member is configured to rotate the first separated array and the second rotary member is configured to rotate the second separated array.

* * * * *